US005801064A

United States Patent [19]
Foresman et al.

[11] Patent Number: 5,801,064
[45] Date of Patent: Sep. 1, 1998

[54] ASSAY METHODS AND REAGENTS FOR DETECTING AUTOANTIBODIES

[76] Inventors: Mark D. Foresman, 6324 Oxford, St. Louis Park, Minn. 55416; Jyotsna Ghai, 3012 Ontario Rd., Little Canada, Minn. 55117; Karel Z. Newman, 6959 Tartan Curve, Eden Prairie, Minn. 55346

[21] Appl. No.: 566,604

[22] Filed: Dec. 4, 1995

[51] Int. Cl.$^6$ .......................... G01N 33/543; C07K 1/00
[52] U.S. Cl. ............................. 436/518; 435/68; 435/70; 435/172.3; 435/235; 435/252.1; 530/350; 530/358
[58] Field of Search ........................ 435/68, 70, 172.3, 435/235, 252.1; 530/350, 358; 436/508, 518

[56] References Cited

U.S. PATENT DOCUMENTS

| | | |
|---|---|---|
| 4,683,195 | 7/1987 | Mullis et al. |
| 4,683,202 | 7/1987 | Mullis |
| 4,946,778 | 8/1990 | Ladner et al. |
| 5,091,513 | 2/1992 | Huston et al. |
| 5,223,409 | 6/1993 | Ladner et al. |
| 5,229,272 | 7/1993 | Paul et al. |
| 5,260,203 | 11/1993 | Ladner et al. |

FOREIGN PATENT DOCUMENTS

| | | |
|---|---|---|
| 0614982 | 3/1994 | European Pat. Off. |
| WO9302198 | 7/1991 | WIPO |
| WO9424560 | 4/1994 | WIPO |

OTHER PUBLICATIONS

Sigma Chemical Company—1992 Catalogue, pp. 1186–1187, 1992.

D. Inbar et al., "Crystallization With Hapten of the Fab Fragment From a Mouse IgA Myeloma Protein With Anti-dinitrophenyl Activity", *Journal of Biological Chemistry*, pp. 6272–6275 (Oct. 25, 1971).

J.S. Huston et al., "Protein Engineering of Antibody Binding Sites: Recovery of Specific Activity in an Anti-digoxin Single-chain $F_v$ Analogue Produced in *Escherichia Coli*", *Proc. Natl. Acad. Sci.*, 85:5879–5883 (1988).

A. Skerra et al., "Assembly of a Functional Immunoglobulin $F_v$ Fragment in *Escherichia Coli*", *Science*, 240:1038–1040 (1988).

J. McCafferty et al., "Phage Antibodies: Filamentous Phage Displaying Antibody Variable Domains", *Nature*, 348:552–554 (1990).

Pluckthun et al., "Properties of $F_v$ and $F_{ab}$ Fragments of the Antibody McPC603 Expressed in *E. Coli*", *Behring Inst. Mitt.*, 87:48–55 (1990).

E. Ben–Chetrit et al., "A 52–kD Protein is a Novel Component of the SS–A/Ro Antigenic Particle", *J. Exp. Med.*, 167:1560 1571 (1988).

R. Porter, "The Hydrolysis of Rabbit g–globulin and Antibodies with Crystalline Papain", *Biochemistry*, 73:119–26.

N. Hilschmann et al., "Amino Acid Sequence Studies with Bence–Jones Proteins", *Proc. Natl. Acad. Sci.*, 53:1403–9 (1965).

W. Huse, "Generation of a Large Combinatorial Library of the Immunoglobulin Repertoire in Phage Lambda", *Science*, 246:1275–81 (1989).

H. Hoogenboom, Multi–subunit Proteins on the Surface of Filamentous Phage: Methodologies for Displaying Antibody (Fab) Heavy and Light Chains, *Nucl. Acids Res.*, 19:4133–7 (1991).

S. Ward, "Binding Activities of a Repertoire Domains Secreted from *Escherichia coli*", *Nature*, 341:544–6 (1989).

D. Inbar et al, "Localization of Antibody–combining Sites Within the Variable Portions of Heavy and Light Chains", *Proc. Natl. Acad. Sci* USA 69:2659–62 (1972).

J. Chirgwin et al, "Isolation of biologically active ribonucleic acid from sources enriched in ribonuclease", *Biochemistry* 18:5294 (1979).

M. Edmonds et al, "Polyadenylic Acid Sequences in the Heterogenous Nuclear RNA and Rapidly–labeled Polyribonosumal RNA of HeLa Cells; Possible Evidence for a Precursor Relationship", *Proc. Natl. Acad. Sci* USA 68:1336 (1972).

H. Aviv et al, "Purification of Biologically Active Globin Messenger RNA by Chromatography on Oligo–thymidylic Acid–cellulose", *Proc. Natl. Acad. Sci* USA 69:1408 1972.

Package insert materials from Pharmacia Biotech kit for Recombinant Phage Antibody System (2 parts).

*Primary Examiner*—James C. Housel
*Assistant Examiner*—Rodney P. Swartz
*Attorney, Agent, or Firm*—Fredrikson & Byron, P.A.

[57] ABSTRACT

Solid phase reagents having immobilized thereon novel single-chain Fv antibodies specific to SS-A/Ro autoantigens have been developed for use in immunoassays to detect the presence or amount of autoantibodies to such autoantigens in a test sample. The solid phase reagents can also be used to purify autoantigen. Diagnostic test kits which contain these single-chain Fv antibodies specific to SS-A/Ro autoantigen useful in immunoassays are also described.

5 Claims, No Drawings

ASSAY METHODS AND REAGENTS FOR DETECTING AUTOANTIBODIES

FIELD OF THE INVENTION

The present invention relates to immunoassays utilizing novel single chain Fv antibody reagents, and more particularly to use of such recombinant single chain Fv antibodies for immobilization of antigens useful in the detection of autoantibodies such as those directed against SS-A/Ro present in test solutions such as patient samples.

BACKGROUND OF THE INVENTION

Autoantibodies to a variety of nuclear antigens have been found in the sera of patients with systemic rheumatic diseases such as Systemic Lupus Erythematosus (SLE) and Sjögren's Syndrome (SS). One such antigen is referred to in the literature as SS-A, Ro or sometimes SS-A/Ro and is a macromolecular complex of two acidic polypeptides (60 kD and 52 kD) and four uridine-rich cytoplasmic RNAs (Y1, Y3, Y4, Y5) ranging from 80 to 112 bases. Autoantibodies specific for SS-A/Ro occur in 24–60% of SLE patients' sera and 85–95% of SS patients' sera.

Methods for detecting autoantibodies to nuclear antigens currently exist and include indirect immunofluorescence and enzyme immunoassays using purified antigen adsorbed on a solid phase. The first method is time consuming, laborious and subjective and; in the case of the second, obtaining purified autoantigens suitable for use in enzyme immunoassays is difficult and significant variations in quality are observed between lots. A reagent which can specifically bind to the functional autoantigen, such as a monoclonal antibody, and capture it to a solid phase to isolate and retain the antigen and/or as a reagent in an immunoassay or be used as a labeled conjugate to identify the relevant autoantibodies would be useful. However, for various reasons, it is extremely difficult to obtain monoclonal antibodies to some of these autoantigens, such as SS-A/Ro using the conventional hybridoma methodology. Most notably, production of antibodies by an animal to immunologically defined self-antigens may be prevented by repressive host mechanisms.

Recently, methods of producing monoclonal antibodies using recombinant DNA and gene amplification techniques to clone antibody genes in bacteria have been described that avoid some of the problems associated with the hybridoma methodology.

Antibodies are proteins made by the immune system in response to a specific antigen or substance which the body deems foreign. All antibodies have a common structure consisting of two identical sets of 25 kD and 50 kD polypeptide chains denoted as light and heavy chains, respectively. The light and heavy chains are held together by disulfide bridges and non-covalent bonds giving rise to a heterodimer possessing functional binding capabilities. Within each of the chains are defined regions referred to as the Variable (V), Joining (J) and Constant (C) regions. The DNA and amino acid sequence of the V region is antigen dependent and have been assumed to be responsible for the binding specificity of individual antibodies. Pairing of the V regions of the heavy and light chains forms an antigen-binding site which recognizes a single antigenic determinant (epitope) of an antigen.

This functional binding domain can be isolated using various molecular techniques, including protease digestion and recombinant expression of the desired fragment containing the binding domain. This fragment is often referred to as the Fab fragment and it contains the V and C regions of both a heavy and light chain of an antibody molecule linked by disulfide bonds. It has been discovered that an even smaller fragment capable of specifically recognizing and binding to an antigen can be created. This fragment often referred to as the Fv portion (or region) consists of the V regions of the antibody light and heavy chains.

With recombinant techniques, single polypeptides have been created including the V regions of the light and heavy chain of an antibody molecule joined by a non-specific linking region. This newly created protein structure is commonly referred to as a single chain Fv (scFv) antibody and will retain its functional antigen recognition and binding capability. However, some properties of such scFv antibodies may differ from the properties of the native antibody. For example, some scFv antibodies will form aggregates, while others may be intrinsically insoluble. Other scFv antibodies may non-specifically adhere to heterogeneous biological and synthetic matrices and thus be inappropriate for use in an immunoassay for a specific substance.

Therefore, the creation of scFv antibodies that specifically bind to autoantigens such as SS-A/Ro and which can be adsorbed on a solid phase and retain their functional antigen-binding capabilities would be useful in immunoassays using autoantigens to detect autoantibodies to those autoantigens in a patient's serum.

SUMMARY OF THE INVENTION

The present invention relates to novel single chain Fv antibody reagents which specifically bind to an autoantigen and the use of such reagents in immunoassays to immobilize the autoantigen to a solid phase.

In one embodiment, the invention relates to the scFv antibodies to autoantigens such as SS-A/Ro. Another embodiment of the invention relates to the use of such scFv antibodies to immobilize autoantigen on a solid phase, thus, the necessity of purifying the autoantigen from a solution of cellular substances may be avoided, as the scFv antibody will specifically bind the autoantigen of interest.

Another embodiment of the invention provides an assay for autoantibodies in a test sample specific for a particular autoantigen wherein scFv antibodies specific for the autoantigen are attached to a solid phase and contacted with a solution containing a predetermined amount of autoantigen for a time and under conditions suitable for autoantigen to bind to the solid phase and then the solid phase is contacted with a test sample for a time and under conditions suitable for an autoantigen/autoantibody complex to form and a labeled reagent comprising a label generating a detectable signal and a specific binding member for the autoantibodies is contacted with said solid phase for a time sufficient for a reaction to occur and wherein the amount of signal detected is an indication of the presence and amount of autoantibodies specific for the autoantigen present in the sample. The autoantigen is preferably the SS-A/Ro autoantigen.

In another embodiment of the invention, the scFv antibodies specific for a particular autoantigen is conjugated to a label generating a detectable signal Yet another embodiment of the invention provides a test kit for use in detecting the presence of autoantibodies to a specific autoantigen in a test sample which test kit includes a solid phase having a scFv antibody specific for the autoantigen immobilized thereon, and preferably wherein the scFv antibody is specific for the SS-A/Ro autoantigen.

Another embodiment of the invention is a method for detecting autoantibodies in a sample comprising the steps of contacting a solid phase to which an scFv antibody specific for an autoantigen has been immobilized with a test sample for a time and under conditions suitable for autoantibodies in the sample to bind to the solid phase, then a solution containing a predetermined amount of an antihuman antibody conjugated is contacted with the solid phase and the amount of label measured. The amount of label detected will be related to the presence or amount of autoantibodies specific to a particular autoantigen present in the test sample.

DETAILED DESCRIPTION

The present invention relates to scFv antibodies specific to a particular autoantigen and their use in assays and test kits, and preferably to scFv antibodies specific to SS-A/Ro autoantigen.

To obtain the scFv antibodies specific to a particular autoantigen, a combinatorial library derived from spleens of NZB mice immunized with bovine SS-A/Ro autoantigen was generated by adapting the techniques for the production of single chain antibodies described in U.S. Pat. No. 4,946,778, the teachings of which are herein incorporated by reference. Briefly, after mRNA was purified from mice immunized with bovine SS-A/Ro autoantigen, immune spleens were removed and total RNA and messenger RNA isolated. Reverse transcriptase and specific primers were used to generate cDNA of antibody V genes and polymerase chain reaction (PCR) was used to generate a scFv-fragment. The resulting scFv fragment was inserted into an appropriate vector, such as the pCANTAB 5E plasmid provided in the Recombinant Phage Antibody System (RPAS) which is available from Pharmacia Biotech using restriction endonuclease digestion and ligation. The resulting recombinant vectors were transformed into a host suitable for recombinant phage production. The desired recombinant phage was then selected from the pool by being subjected to three rounds of phage enrichment panning on a SS-A/Ro autoantigen presenting solid phase.

A particularly preferred scFv antibody specific for the SS-A/Ro autoantigen was obtained. This antibody can be produced by isopropyl-β-D-thiogalactopyranoside (IPTG, Kodak-IBI) induction of the recombinant plasmid contained in the E. coli bacteria culture deposited at the American Type Culture Collection, 12301 Parklawn Drive, Rockville, Md. on Dec. 1, 1995, and has been assigned ATCC No. 69958 (E. coli cell line) and ATCC 69959 (plasmid).

Single chain Fv antibodies specific for the SS-A/Ro autoantigen may be used for any diagnostic assay application as a capture reagent immobilized on a solid phase or attached to a detectable label. After obtaining the recombinant scFv antibodies as described herein, the antibodies may be employed for use in an assay in the form of a kit comprising a solid phase to which the scFv antibodies are immobilized with one or more containers such as vials, or reagent packages having multiple compartments, with each container or compartment containing a separate reagent employed in the assay.

"Solid phases" as used herein are well known in the art and refers to an insoluble material to which one component of the assay may be found and include the walls of test tubes or wells of a microtiter plate, polystyrene beads, magnetic beads, nitrocellulose strips, membranes, latex microparticles, and others and made of hydrocarbon polymers such as polystyrene and polypropylene, glass, metals, gels or other materials. The "solid phase" is not critical and can be selected by one skilled in the art.

Suitable methods for immobilizing antibodies and proteins such as the scFv antibodies of the invention on solid phases include ionic, hydrophobic, covalent interactions and the like. The solid phase can be chosen for its ability to attract and immobilize the scFv antibodies or the solid phase can retain a receptor which has the ability to immobilize the scFv antibodies indirectly.

"Labeled reagent" as used herein refers to a conjugate of an scFv antibody of the invention, antibody or other specific binder for the autoantibodies being assayed, such as an anti-IgG or anti-IgM antibody, with a compound capable of generating a detectable signal such as an enzyme, radioisotope, chromophore, luminescent compounds such as fluorescein and rhodamine, chemiluminescent compounds and direct visual labels. Examples of enzymes include horseradish peroxidase, alkaline phosphatase, beta-galactosidase, and the like. The selection of a particular label is not critical but will be capable of producing a detectable signal either by itself or in conjunction with one or more reagents. Detection of signal might also be accomplished with or without a label using biosensors which measures changes in electrical conductance, mass or resonance.

"Test sample" as used herein means any variety of biological samples which can be tested by the methods of the present invention described herein and include human and animal body fluids such as whole blood, serum, and plasma or other tissue from humans or animals suspected of containing autoantibodies to a particular autoantigen of interest.

In an assay of the invention, the scFv antibody of the invention is immobilized on a solid phase. Then a solution containing a predetermined amount of SS-A/Ro autoantigen is contacted and incubated with the solid phase so that the SS-A/Ro autoantigen will form a complex with the scFv antibody and become affixed to the solid phase. After the complex has formed, test sample is contacted with the solid phase to which the SS-A/Ro antigen has been affixed and if autoantibodies are present in the sample, they will complex with the autoantigen and also become immobilized on the solid phase. After the complexes are formed, the solid phase is separated from the unbound materials and reagents and washed. Then the solid phase is contacted with a labeled reagent and incubated until labeled reagent has bound to any autoantibodies bound to the solid phase. The presence or amount of autoantibodies in the test sample is then determined by detecting the signal generated by the retained label.

In another assay of the invention the scFv antibody is conjugated to a label compound and can be used as a labeled reagent in an assay. Depending on the label chosen for use in the assay the conjugation technique used to make the reagent will vary. Such conjugation techniques are well known to the art. In the case of an enzyme label the enzyme is often conjugated to the antibody by means of glutaraldehyde or periodate. In an assay using a labeled scFv antibody comprises contacting a solid phase having immobilized thereon a specific binding member for antibodies. All antibodies in the test sample will form complexes with the specific binding member and affix the antibodies to the solid phase. Then a solution containing a predetermined amount of SS-A/Ro autoantigen is contacted to the solid phase to which the antibodies in the test sample are affixed. SS-A/Ro autoantigen will complex with those autoantibodies on the solid phase specific for that autoantigen. Then the solid phase will be separated from unbound materials and reagents and the labeled scFv antibody reagent added and allowed to complex with the bound SS-A/Ro autoantigen. The presence or amount of autoantibody present in the sample specific for the SS-A/Ro autoantigen can then be determined by measuring the amount of signal generated by the label.

SS-A/Ro autoantigen fractions useful with the assays of the invention are commercially available from companies such as Immunovision, or can be extracted and isolated from a variety of sources such as bovine liver, calf thymus, HeLa cells, human spleen cells, human peripheral blood lymphocytes and the like.

In another embodiment of the invention, the scFv antibodies can be used to isolate and purify SS-A/Ro autoantigen from extracts of human/animal cells by passing the extracts over scFv antibody immobilized on a solid phase, such as a column. The flow-through and eluate can then be screened by enzyme immunoassay for immunoreactive autoantigen.

The invention may be better understood by reference to the following non-limiting examples.

EXAMPLE 1

Preparation of Single Chain Fv Antibodies to SS-A/Ro Autoantigen mRNA Purification Twenty-six week old female NZB/J mice were immunized on a biweekly basis with a 5 microgram (ug)/dose of bovine SS-A/Ro antigen (obtained from Immunovision) in complete Freund's adjuvant (CFA, initial two injections) and incomplete Freund's adjuvant (ICFA) by the subcutaneous route. Serum samples from these mice were screened by an enzyme immunoassay (EIA) utilizing human Ro/La sera to determine the immune status of the mice. Briefly, the EIA was performed by coating a 96 well microtiter plate with goat anti-mouse IgG+M antiserum followed by the addition of diluted sample mouse sera to the plate; unbound antibodies were washed away. A solution containing bovine SS-A/Ro autoantigen was then contacted to the plate and allowed to react with antibodies present in the sample specific for the autoantigen. After any unbound material was washed away, human anti-Ro serum was added to the plate. Unbound antibodies were washed away and a known amount of goat anti-human IgG+M-horseradish peroxidase conjugate added and following a wash step substrate was added. The amount of signal generated from the reaction between horseradish peroxidase and its substrate indicated whether the sample mouse sera contained autoantibodies specific for the SS-A/Ro autoantigen. Mice exhibiting an elevated titer of antibodies to bovine SS-A/Ro were selected as the source of immune RNA.

Immune mice were sacrificed by cervical dislocation and the spleens surgically removed. Spleens were immediately frozen in liquid nitrogen. The frozen splenic tissue was placed in guanidinium solution (guanidine isothioynate solution: 4M guanidine isothiocyanate, 50 mM Tris-HCl pH 7.5, 25 mM EDTA containing 5% β-mercaptoethanol) and immediately homogenized. The homogenate was centrifuged at 12,000×g for 10 min. at 12° C. Supernatant was collected and mixed with one-tenth volume of 20% solution of a detergent. This mixture was heated 65° C. for 2 min. The solution was extracted sequentially with an equal volume of 25:24:1 phenol/chloroform/isoamyl alcohol, then with 24:1 chloroform/isoamyl alcohol. The extract was centrifuged 15 min. 15,800×g at 4° C., the pellet was mixed with one-tenth volume of 3M sodium acetate and 2.5 volumes ethanol, and allowed to precipitate at −70° C. for 20 min.

The RNA fraction was pelleted by centrifugation 15 min. at 15,800×g, 4° C., and mRNA was isolated by affinity purification of mRNA on oligo(dT)cellulose obtained using the FastTrack® mRNA Isolation Kit commercially available kit from Invitrogen of San Diego, Calif. (hereinafter all references to FastTrack® reagents refer to reagents available in this kit). Other similar mRNA isolation kits are commercially available and the methods of isolating mRNA are well known to those skilled in the art. Briefly, the RNA pellet was resuspended in detergent-based buffer containing RNase/Protein Degrader, specifically the Fast Track® Lysis buffer. The preparation was sheered by repeated passage through an 18 gauge needle and then a 21 gauge needle on a sterile polypropylene 10 ml syringe. This preparation was then incubated for 30 min. at 45° C. in a slow (range: 100–150 rpm) shaking water bath. The NaCl concentration of the lysate was adjusted to 0.5M. Oligo(dT)cellulose was added to the lysate and rocked gently at room temperature for 60 min. The Oligo(dT)cellulose was pelleted by centrifugation at room temperature at 3,000×g for 5 min. After aspirating the supernatant, the Oligo(dT)cellulose was resuspended in 20 ml of high salt buffer, Fast Track® Binding buffer and washed with 10 ml of Fast Track® Binding buffer and then three times with 10 ml of low salt buffer, Fast Track® Low Salt Wash Buffer. After the last wash, the Oligo(dT)cellulose was resuspended in Fast Track® Low salt wash buffer at a final volume of 0.8 ml. The sample was transferred into a spin-column and centrifuged at room temperature for 10 sec. at 4,000×g. The sample was washed three times with Fast Track® Low Salt Wash Buffer. The mRNA was eluted by twice mixing the cellulose in the absence of salt in 200 microliters (ul) of Fast Track®. Elution buffer and centrifuging for 10 seconds. The mRNA was precipitated with 0.15 volume of 2M sodium acetate and 2.5 volumes of 100% ethanol, and frozen at −70° C. until solid. The mRNA was pelleted by centrifugation at 16,000×g for 15 min. at 4° C. and ethanol removed. This mRNA pellet was resuspended in 20–50 ml of Fast Track® Elution buffer and stored at −70° C. From two spleens approximately 5.5 ug of mRNA was isolated with an $A_{260}/A_{280}$ ratio of 1.74.

First-strand cDNA Synthesis and Primary PCR Amplification

Two identical first-strand cDNA reactions were set up, one for the heavy chain and the other for the light chain, using the techniques described in the Recombinant Phage Antibody System (RPAS), a kit available from Pharmacia Biotech. The mRNA was heated at 65° C. for 10 min. and cooled immediately on ice. It was then mixed with RNase-free water, primed first-strand mix (containing M-MuLV reverse transcriptase, random hexadeoxyribonucleotides [pd(N)$_6$], RNase inhibitor, RNase/DNase-free BSA, dATP, dTTP, dCTP, and dGTP in aqueous buffer), and 200 mM dithiothreitol (DTT) solution and incubated at 37° C. for 1 hour.

The resulting first-strand cDNA was used as a template for PCR amplification of antibody heavy and light chain cDNAs. For the light chain reaction, the first-strand cDNA was incubated with 10 variable light chain primers of both 5' and 3' orientation, available from Pharmacia Biotech as Light Primer mix and sterile distilled water at 95° C. for 5 min. prior to the addition of Taq DNA polymerase, commercially available from a variety of sources. The heavy chain reaction consisted of first-strand cDNA, Heavy chain primer 1 (5' heavy chain primer or upstream primer), Heavy chain primer 2 (3' heavy chain primer or downstream primer), and sterile distilled water heated at 95° C. for 5 min. prior to the addition of Taq DNA polymerase. The Taq DNA polymerase was added under mineral oil and the reactions incubated for 30 cycles: 94° C. for 1 min.; 55° C. for 2 min.; 72° C. for 2 min. and extended at 72° C. for 10 min. in a Perkin-Elmer-Cetus DNA Thermal Cycler 480. Reagents for the amplification reactions are available from Perkin-Elmer Cetus and the PCR process is described in U.S. Pat. Nos. 4,683,195 and 4,683,202.

Purification of Primary PCR Products

The primary PCR products were purified by electrophoresis using a 1.5% agarose Tris-acetate-EDTA (TAE)-buffered gel. The DNA bands of approximately 340 base pairs (heavy chain) and 325 bps (light chain) were excised from the gel and placed in separate agarose gel columns provided with the RPAS kit, however, other commercially available purification systems may be used. . The columns were centrifuged at 2,000 rpm for 2 min. to elute the DNA. The purified heavy and light chain DNA products were quantified by electrophoresis using ethidium bromide-stained samples alongside a $V_H$ marker of known concentration, in a 1.5% agarose Tris-borate-EDTA (TBE)-buffered gel to determine the optimal amount of each to be added to the assembly reaction.

Assembly and Fill-In Reaction of scFv and Secondary PCR Amplification

Assembly of the purified heavy and light chain DNA products into the scFv antibody required addition of approximately equimolar amounts of heavy chain PCR product, light chain PCR product, and Linker-Primer mix (equimolar mixture of 3' heavy and 5' light linker primers) in 10×PCR buffer (Invitrogen) containing 2.5 mM dNTP mix, 25 mM $MgCl_2$, Taq DNA polymerase, and sterile distilled water. The reaction was overlaid with mineral oil and incubated for 7 cycles: 94° C. for 1 min.; 63° C. for 4 min.

A second PCR amplification reaction was done to amplify the assembled antibody scFv DNA fragments with a set of oligonucleotide primers to introduce restriction sites for cloning into the pCANTAB 5E vector. This reaction required addition of more Taq DNA polymerase, 10×PCR buffer, dNTP mix, RS primer mix (mixture of 5' heavy chain primer with Sfi I site and 3' light chain primer with Not I site) and sterile distilled water beneath the mineral oil to complete the assembly and fill-in reaction. The reaction mixture was incubated for 30 cycles: 94° C. for 1 min.; 55° C. for 2 min.; 72° C. for 2 min. and extended at 72° C. for 10 min. A 750 bp assembled scFv product was purified from the PCR mix by chromatography through a spin column at 800×g for 20 sec.

Restriction Digestion

The scFv fragment was sequentially digested with Sfi I and Not I restriction DNA endonucleases in preparation for ligation into the pCANTAB 5E vector. For Sfi I digestion, the column-purified assembled PCR product was mixed with 10×Sfi I buffer (Boehringer Mannheim), 40–50 units of Sfi I (Boehringer Mannheim), and sterile distilled water and incubated at 50° C. overnight. The digested scFv DNA was desalted using a silica bead affinity purification method. For Not I digestion, the purified scFv DNA was mixed with 5M NaCl, 10×Not I buffer (Boehringer Mannheim), 75–100 units of Not I (Boehringer Mannheim), and sterile distilled water and incubated overnight at 37° C. The digested scFv DNA was again desalted by using the silica bead affinity purification method.

Ligation of scFv Gene into pCANTAB 5E

The ligation reaction of scFv and pCANTAB 5E was set up by mixing the scFv gene, polyethylene glycol buffer, pCANTAB 5E provided in the RPAS kit (100 ng), 3.75 mM ATP, and T4 DNA ligase (5–7 units, Boehringer Mannheim), and incubated at 16° C. for 1 hour.

Electro-transformation

The ligated pXRo (anti-Ro scFv in pCANTAB 5E) was electroporated into Electro-Competent™ MV1190 E. coli cells (BioRad) using the Electroporator II (Invitrogen). The frozen MV1190 E. coli cells were thawed on ice and mixed with 2 ul of pXRo in a pre-chilled 0.1 cm cuvette. The cells were pulsed with 50 mF, 1.8 kV at 100 ohms. The cells were immediately mixed with 1 ml of fresh media containing 2% tryptone, 0.5% yeast extract 10 uM NaCl, 2.5 mM KCl, 10 mM $MgCl_2$, 10 mM $MgSO_4$ and 20 mM glucose (SOC media) and cultured at 37° C. for 1 hour while gently shaking at 150 rpm. The cells were then plated on SOBAG (SOC media containing ampicillin and glucose) agar and incubated overnight at 30° C. The transformation efficiency was calculated from the control plasmid, pTZ18U (BioRad), at $1.21 \times 10^8$ cfu/ug with a background of $8.8 \times 10^3$ cfu/ug of pCANTAB 5E.

Rescue of Recombinant Antibody Phage Library

The ampicillin and glucose plate cultures for example were flooded with 5 ml of 2×YT media. Colonies were resuspended with a sterile glass spreader and the cells cultured at 37° C. and 250 rpm in 2×YT media containing 100 ug/ml ampicillin and 2% glucose at an $A_{600}$ of 0.3. After the culture achieved an $A_{600}$ of 0.7, the cells were inoculated with $2.5 \times 10^9$ pfu of helper phage, M13K07, and incubated for 30 min. at 30° C., 150 rpm followed by 250 rpm for an additional 30 min. The cells were then pelleted by centrifugation at 800×g for 10 min. and diluted 5 fold in 2×YT media containing 100 ug/ml ampicillin and 50 ug/ml kanamycin without glucose. The culture was incubated overnight at 37° C. at 250 rpm. Following the overnight incubation, the cells were removed by centrifugation at 1,000×g for 10 min. The supernatant containing the rescued phage was saved at 4° C. or used immediately for panning against antigen.

Titering Recombinant Phage

Rescued recombinant phage were titered by infecting log-phase E. coli TG1 cells. Log-phase E. coli TG1 cells were prepared by culturing a single colony from a minimal media plate and culturing it in 2×YT (yeast extract, tryptone) media until an $A_{600}$ of 0.5–0.7 was achieved. Serial ten-fold dilution of the recombinant phage were prepared in 2×YT media. The diluted phage (100 ul) was mixed with log-phase TG1 cells (200 ul) and incubated with occasional gentle agitation for 30 min. at 37° C. Cells were then plated on ampicillin and glucose agar and incubated overnight at 30° C. Ampicillin-resistant colonies were counted and the titer of recombinant phage was calculated. Typically titers>$1 \times 10^{12}$ cfu/ml were found.

Panning to Select for Antigen-positive Recombinant Phage Antibodies

Antigen-coated 25 $cm^2$ tissue culture flasks were prepared by incubating 10 units/ml of SS-A/Ro autoantigen in carbonate bicarbonate buffer, pH 9.6 at 4° C. overnight. The flasks were then washed 3 times with PBS, blocked with 2% nonfat dry milk/PBS (blocking buffer) for 1 hour at room temperature and washed 3 times with PBS. The rescued pXRo phage supernatant (titer>$1 \times 10^9$ pfu/ml) was mixed with an equal volume of blocking buffer containing 0.1%

Triton X-100 (Sigma) for 15 min. The blocked recombinant phage supernatant (10 ml) was added to the flask and incubated for 2 hours at 37° C. in a humidified chamber. Following panning the phage supernatant was poured off and the flask was first washed 20 times with PBS and then 20 times with PBS containing 0.1% Tween 20 (Sigma).

Reinfection of *E. coli* with Enriched Phage Clones

Log-phase *E. coli* TG1 cells were prepared by culturing a single colony from a minimal media plate in 10 ml of 2×YT media until an $A_{600}$ of 0.3 was achieved. The entire TG1 culture was added to the phage-absorbed antigen-coated flask and incubated at 37° C. for 1 hour. Ten-fold dilutions of the cells were prepared and plated on ampicillin and glucose agar (100 ml/plate). The plates were incubated overnight at 30° C. The panned anti-SS-A/Ro phagmid library ($>1\times10^3$ cfu/plate) was scraped from the ampicillin and glucose plate as above and rescued as described above prior to another round of antigen panning and reinfection. The library was subjected to a total of three rounds of enrichment prior to microtiter plate rescue of individual clones.

Microtiter Plate Rescue of Enriched Phage Clones

Individual colonies of the tertiary panned pXRo phagemid library were transferred from ampicillin and glucose agar plates to separate wells in a sterile 96 well microtiter plate containing 100 ul/well of 2×YT media containing 100 ug/ml ampicillin and 2% glucose (2×YT-AG). The plate was incubated overnight at 30° C. while shaking at 150 rpm. Microtiter plate rescue was set up by transferring 25 ul of cell-saturated culture/well from the master plate to a sterile 96 well V-bottom plate (Costar) using a Transplate cartridge in the Transplate 96™ apparatus (Costar). To each well, 200 ul of 2×YT-AG media containing $5\times10^8$ pfu/ml of M13K07 helper phage was added and the plate was incubated for 2 hours at 37° C. while shaking at 150 rpm. Robust growth was indicated by the turbid cultures. To pellet the cells and replace the media, the plate was centrifuged at 800×g for 10 min. at room temperature. The supernatants were removed using a Transplate cartridge in the Transplate 96™ apparatus. The cells were resuspended in 200 ul/well of 2×YT media containing 100 ug/ml ampicillin and 50 ug/ml kanamycin and cultured overnight at 37° C. while shaking at 150 rpm.

Enzyme Immunoassay of Recombinant Phage Antibodies

Antigen-coated microtiter plates were prepared as follows. Polyvinyl carbonate 96 well microtiter plates (Falcon) were coated with 10 units/ml of SS-A/Ro autoantigen or 10 ug/ml of BSA (Sigma) as a control antigen in carbonate bicarbonate buffer, pH 9.6 at 4° C. overnight. The plates were washed 3 times with saline, 0.01% Thimerosal, 0.1% Tween 20 (STT), and blocked with 3% nonfat dry milk/PBS (blocking buffer) for 1 hour at room temperature. The plates were washed again as above and then the phage supernatants added (200 ul/well). Supernatants from the microtiter plate rescued pXRo tertiary phage clones were harvested, incubated for 15 min. at room temperature with an equal volume of 3% nonfat dry milk/PBS containing 0.1% Triton X-100, transferred to an antigen-coated microtiter plate and incubated overnight at room temperature. The plates were washed 3 times and sheep anti-M13-horseradish peroxidase conjugate (1:2500, Pharmacia) in blocking buffer was added. The conjugate was incubated on the plates for 1 hour at room temperature. The plates were washed 4 times as described above before the addition of substrate. The 2',2'-azino-bis(3-ethylbenzthiazoline-6-sulphonic acid) diammonium (ABTS, Kirkegaard and Perry Laboratories) substrate was prepared by a 1:1 mixture with $H_2O_2$ solution (Kirkegaard and Perry Laboratories). The substrate was added to each well and incubated at room temperature for >20 min. Substrate conversion was measured on an LP 400 microtiter plate reader (Diagnostics Pasteur) at 405 nm. A total of 88 clone supernatants containing rescued phage were screened by this method. Seventeen gave a signal greater than the signal obtained with the vector control (shown in Table 1 as pCANTAB 5E). Table 1 shows representative data for three of the 17 clones. Readings of 0.150 or greater were indicative of phage-displayed scFv antibodies which could bind to bovine SS-A/Ro. In the table, Ro sera was used as a positive control of antibodies specific for SS-A/Ro. Normal human sera (NHS) was used as a negative control of human antibodies to determine whether non-specific binding is occurring.

TABLE 1

| ENZYME IMMUNOASSAY OF pXRO PHAGE ANTIBODIES | |
|---|---|
| Sample | O.D. 405 nm |
| Ro sera | 0.604 |
| NHS | 0.084 |
| pCANTAB 5E | 0.101 |
| clone 26 | 0.271 |
| clone 58 | 0.173 |
| clone 73 | 0.175 |

Infection of HB2151 Cells

Recombinant antibody clones identified as positive for antigen recognition by EIA were used to infect *E. coli* HB2151 cells in order to produce soluble scFv antibodies. Log-phase HB2151 cells were prepared by culturing a single colony from a minimal media plate and culturing it in 2×YT media until an $A_{600}$ of 0.3–0.5 was achieved. A 200 ul culture of HB2151 cells was inoculated with 1 ul of SS-A/Ro-positive recombinant antibody clone supernatant and incubated for 30 min. at 37° C. with occasional mixing. The culture was plated on ampicillin and glucose-nalidixic acid (100 ug/ml) agar overnight at 30° C. All of the clones produced colonies following incubation.

Production of Soluble scFv Antibodies

Soluble anti-Ro scFv antibodies were produced by transferring a transformed colony of HB2151 cells from ampicillin and glucose-nalidixic acid agar into 5 ml super broth media with 0.3% tryptone, 2% yeast extract, NaCl 100 mM (SB) media containing 100 ug/ml ampicillin and 2% glucose (SB-AG) and incubating overnight at 30° C. while shaking at 250 rpm. The overnight culture was added to 50 ml of SB-AG media and incubated at 30° C. for 1 hour. The cells were pelleted by centrifugation at 1,500×g for 15 min. at room temperature in a SM-24 rotor (Sorvall) and RC-5B centrifuge (Sorvall). After removing the supernatant, the cells were resuspended in 50 ml of SB media containing 100 mg/ml ampicillin and 1 mM isopropyl-b-D-thiogalactopyranoside (IPTG, Kodak-IBI), and incubated for 3 hours at 30° C. at 250 rpm. The culture was divided into two separate tubes and centrifuged at 1,500×g for 15 min. at room temperature. The supernatant was filtered through a 0.8 um membrane and stored at 4° C. until assayed. The duplicate cell pellets were used to prepare respective periplasmic and a whole cell extracts. The periplasmic extract was prepared by resuspending the cell pellet in 0.5 ml of PBS containing 1 mM EDTA and incubating on ice for 10 min. The resuspended cells were centrifuged at 15,800×g in an Eppendorf 5402 refrigerated microcentrifuge at 4° C. for 10 min. The supernatant containing the periplasmic extract was removed from the pellet and stored at −20° C. until assayed. The whole cell extract was prepared by resuspending the second pellet in 0.5 ml of PBS and boiling for 5 min. The resuspended cells were centrifuged at 15,800×g in an Eppendorf 5402 refrigerated microcentrifuge at 4° C. for 10 min. The supernatant containing the whole cell extract was removed from the pellet and stored at −20° C. until assayed.

Enzyme Immunoassay of Soluble Recombinant scFv Antibodies

Antigen-coated microtiter plates were prepared as follows. Polyvinyl carbonate 96 well microtiter plates (Falcon) were coated with 10 units/ml of Ro in carbonate bicarbonate buffer, pH 9.6 at 4° C. overnight. The plates were washed 3 times with saline, 0.01% Thimerosal, 0.1% Tween 20 (STT) and blocked with 10% nonfat dry milk/PBS (blocking buffer) for 1 hour at room temperature. The plates were washed again as above and then the phage supernatants were added (200 ul/well). The supernatants and extracts (100 ul/well) were blocked for 15 min. at room temperature by adding an equal volume of 10% nonfat dry milk/PBS containing 0.05% Tween 20 (BBT). The blocked supernatants and extracts were transferred to an antigen-coated microtiter plate and incubated for 1 hour at room temperature. The plates were washed 3 times with STT. Mouse anti-E Tag antibody-horse radish peroxidase conjugate (1:10,000, Pharmacia) in 5% nonfat dry milk/PBS containing 0.05% Tween 20 was added. The conjugate was incubated on the plates for 1 hour at room temperature. The plates were washed 4 times as above. The ABTS substrate was added to each well and incubated at room temperature for >20 min. Substrate conversion was measured on an LP 400 microtiter plate reader at 405 nm. The seventeen clones identified above were further screened on SS-A/Ro. These results indicate that the scFv antibodies without the bacteriophage bound to SS-A/Ro. As above, Ro sera was used as a positive control, NHS was used as a negative control.

TABLE 2

| ENZYME IMMUNOASSAY OF pXRO SOLUBLE SCFV ANTIBODIES | |
|---|---|
| Sample | O.D. 405 nm |
| Ro sera | 0.328 |
| NHS | 0.058 |
| clone 8 | 0.101 |
| clone 16 | 0.753 |
| clone 19 | 0.098 |
| clone 21 | 0.622 |
| clone 24 | 0.671 |
| clone 26 | 0.512 |
| clone 30 | 0.196 |
| clone 35 | 0.488 |
| clone 58 | 0.585 |
| clone 60 | 0.422 |
| clone 61 | 0.521 |
| clone 62 | 0.411 |
| clone 73 | 0.626 |
| clone 77 | 0.468 |
| clone 80 | 0.298 |

TABLE 2-continued

| ENZYME IMMUNOASSAY OF pXRO SOLUBLE SCFV ANTIBODIES | |
|---|---|
| Sample | O.D. 405 nm |
| clone 87 | 0.467 |
| clone 88 | 0.063 |

EXAMPLE 2

Sandwich Enzyme Immunoassay of Soluble Recombinant scFv Antibodies

Antibody-coated microtiter plates were prepared as follows. Polyvinyl carbonate 96 well microtiter plates were coated with 2 ug/ml of anti-E Tag antibody in 10 mM phosphate-buffered saline (PBS), pH 7.4 at 4° C. overnight. The plates were washed 3 times with STT and blocked with 10% nonfat dry milk/PBS (blocking buffer, BB) for 1 hour at room temperature. The bacterial supernatants containing scFv antibody were pre-absorbed by incubation at room temperature for 15 min. with an equal volume of BBT. The pre-absorbed supernatants were then added to the plate (100 ul/well) and incubated for 1 hour at room temperature. The plates were washed 3 times with STT and then SS-A/Ro autoantigen was added at 2 units/ml in saline for 1 hour at room temperature. The plates were washed 3 times with STT and then human anti-Ro sera or normal human sera (100 ul/well) was added at a 1:50 dilution in 50% BBT containing 25% vector control, pCANTAB 5E, bacterial supernatant and 50 ug/ml of normal mouse IgG (Scantibodies Laboratories) for 1 hour at room temperature. The plates were washed 3 times with STT and then goat anti-human IgG+M-horse radish peroxidase conjugate containing 50 ug/ml of normal mouse IgG was added (100 ul/well) for 1 hour at room temperature. The plates were washed 4 times with STT. The ABTS substrate was added to each well and incubated at room temperature for >20 min. Substrate conversion was measured on an LP 400 microtiter plate reader at 405 nm. In this Example the ability of the cloned soluble scFv antibodies to bind to SS-A/Ro autoantigen and present it in a functional manner (recognizable to autoantibodies in a sample) to human anti-SS-A/Ro antibodies. Each of the thirteen clones identified above expressed scFv antibodies that were able to present SS-A/Ro to human anti-Ro sera but not NHS. Only the results for clones 21, 58, and 73 are shown in Table 3, however, similar results were obtained with clones 16, 24, 26, 35, 60,61, 62, 77, 80 and 87.

TABLE 3

| SANDWICH ENZYME IMMUNOASSAYS OF SOLUBLE pXRo SCFV AND ANTI-SS-A/RO SERA | | |
|---|---|---|
| | O.D. 405 nm | |
| Sample | Anti-SS-A/Ro | NHS |
| pCANTAB 5E | 0.074 | 0.098 |
| clone 21 | 0.315 | 0.07 |
| clone 58 | 0.365 | 0.089 |
| clone 73 | 0.269 | 0.086 |

EXAMPLE 3

Immunoprecipitation of scFv Antibodies

The SS-A/Ro autoantigen (100 ug) was iodinated with $Na^{125}I$ (1 mCi, Nordion International) using a single IODO- BEAD® nonporous polystyrene bead (a registered trademark of Pierce Chemical) N-chloro-benzenesulfonamide (sodium salt) immobilized iodinating reagent (Pierce Chemical). The IODO-BEAD® bead was washed with 500 ul of iodination buffer (100 mM potassium sodium phosphate buffer, pH 7.3), dried on a paper towel, and added to the solution of carrier free $Na^{125}I$ in iodination buffer for 5 min. at room temperature. The antigen in 100 ul of 10 mM Tris, 530 mM NaCl, 0.02% $NaN_3$ buffer was added to the $Na^{125}I$ and incubated for 15 min. on ice. The reaction was stopped by removing the IODO-BEAD® bead. Gel filtration was performed to remove excess $Na^{125}I$ or unincorporated $^{125}I_2$ from the iodinated antigen using an anion exchange resin, AG 1-X4 acetate form (200–400 mesh, BioRad) and elution buffer, 100 mM potassium sodium phosphate containing 1% BSA and 0.1% $NaN_3$, pH 7.3. Fractions were collected and pooled that contained the majority of the cpm (total $2.6 \times 10^8$ cpm) which represented 165 microCi of incorporated $^{125}I$. The iodinated antigen was stored at $-20°$ C. until immunoprecipitated.

The iodinated SS-A/Ro is immunoprecipitated with Protein G-agarose (Scheicher and Schuell) sensitized with anti-E Tag antibody (10 ug/ml of gel) overnight at 4° C., washed with 100 mM Tris-Cl, pH 8.0 (wash buffer), and then incubated with scFv antibody containing bacterial supernatants pre-absorbed with 10% nonfat dry milk/100 mM Tris-Cl for 1 hour at room temperature. The sensitized agarose was washed with wash buffer and iodinated SS-A/Ro (25 microCi) added for 2 hour at 4° C. Unbound antigen is removed by washing 3 times with wash buffer.

For SDS-PAGE analysis of the immunoprecipitate, 2×SDS sample diluent (Sigma) is added to the pellet, resuspended thoroughly, and heated at 80° C. for 3 min. The agarose is spun out for 5 min. and the supernatant loaded on an SDS gel with appropriate pre-stained size markers. After the gel is done, the proteins are fixed, the gel dried, and then exposed to X-ray film (Kodak).

Each of the thirteen clones was able to immunoprecipate $^{125}I$-labelled SS-A/Ro autoantigen as determined by gel electrophoresis separation of the proteins and Coomassie Blue staining of the proteins as well as autoradiography of the dried gel which revealed radioactivity which corresponded to the position of SS-A/Ro 60 kD and 52 kD.

While preferred embodiments of the present invention have been described, it should be understood that various changes, adaptations and modifications may be made therein without departing from the spirit of the invention and the scope of the appended claims.

What is claimed is:

1. A method for the in vitro detection of the presence or amount of autoantibodies specific to an autoantigen in a test sample comprising: contacting a solution containing a predetermined amount of the autoantigen with a solid phase to which scFv antibody specific to the autoantigen is immobilized, then contacting the sample with the solid phase to which the autoantigen has been captured and allowing the autoantibodies present in the test sample to bind to the captured autoantigen, contacting the solid phase to which autoantibodies are bound with a predetermined amount of a labeled reagent that will specifically bind to the bound autoantibodies and detecting the amount of label bound to the autoantibodies, where the autoantigen is SS-A/Ro.

2. A single chain Fv antibody capable of specifically binding to SS-A/Ro autoantigen.

3. A solid phase for use in an assay for determining the presence or amount of autoantibodies specific for an autoantigen in a test sample comprising a solid surface having immobilized thereon a single chain Fv antibody capable of specifically binding the autoantigen to immobilize the autoantigen on the solid phase, where the autoantigen is SS-A/Ro autoantigen.

4. A method of isolating SS-A/Ro autoantigen from a solution containing a mixture of cellular materials comprising contacting a solid phase having a scFv antibody specific for SS-A/Ro autoantigen immobilized thereon with the solution for a time and under suitable conditions to allow the SS-A/Ro autoantigen present in the solution to bind to the scFv antibody immobilized on the solid phase.

5. A test kit for use in determining the presence or amount of autoantibodies specific for SS-A/Ro autoantigen in a test sample comprising the solid phase of claim 3.

* * * * *